(12) United States Patent
Alwan et al.

(10) Patent No.: US 7,826,983 B2
(45) Date of Patent: Nov. 2, 2010

(54) INSTRUMENTED MOBILITY ASSISTANCE DEVICE

(76) Inventors: Majd Alwan, 479 Rolling Valley Ct., Charlottesville, VA (US) 22902; Glenn S. Wasson, 1415 Edmond Dr., Crozet, VA (US) 22932; Pradip N. Sheth, 106 Cannon Pl., Charlottesville, VA (US) 22901; Alexandre Ledoux, 943 Saint Charles Ave., Charlottesville, VA (US) 22901; Cunjun Huang, 395 Ano Nuevo Ave., #1012, Sunnyvale, CA (US) 94085

( * ) Notice: Subject to any disclaimer, the term of this patent is extended or adjusted under 35 U.S.C. 154(b) by 147 days.

(21) Appl. No.: 11/650,361

(22) Filed: Jan. 5, 2007

(65) Prior Publication Data

US 2007/0233403 A1  Oct. 4, 2007

Related U.S. Application Data

(63) Continuation of application No. PCT/US2005/024072, filed on Jul. 7, 2005.

(60) Provisional application No. 60/586,107, filed on Jul. 7, 2004.

(51) Int. Cl.
G01C 22/00 (2006.01)
G06F 19/00 (2006.01)

(52) U.S. Cl. .................................................. 702/33

(58) Field of Classification Search ............... 702/33, 702/178, 160; 482/8, 9, 52; 434/236, 247; 128/80; 137/67; 135/66, 67; 280/87.041
See application file for complete search history.

(56) References Cited

U.S. PATENT DOCUMENTS 4,760,850 A * 8/1988 Phillips et al. ................ 607/49

(Continued)

FOREIGN PATENT DOCUMENTS

EP 1260201 A1 11/2002

(Continued)

OTHER PUBLICATIONS

Wasson, Glenn et al., "User Intent in a Shared Control Framework for Pedestrian Mobility Aids", IEEE International Conference on Intelligent Robots and Systems (IROS), 2003, 6 pages.*

(Continued)

*Primary Examiner*—Cindy H Khuu
(74) *Attorney, Agent, or Firm*—Brake Hughes Bellermann LLP

(57) ABSTRACT

Various implementations are disclosed for an instrumented mobility assistance device, such as an instrumented walker. The device includes an attached sensor that is operable to convert an operational action of a user of the mobility assistance device into a sensor signal. A use analyzer is operable to relate the sensor signal to a contact attribute associated with a contact of the user of the mobility assistance device with an underlying surface. The use analyzer is further operable to determine a gait characteristic of the user, based on the contact attribute. The sensor may include a force or moment sensor. The contact attribute may include a foot-initial contact, or a foot-off contact. In this way, gait characteristics of the user may be determined during normal operation of the instrumented device. Also, the sensor may be used to determine a stability measure associated with the device.

25 Claims, 7 Drawing Sheets

U.S. PATENT DOCUMENTS

| | | | | |
|---|---|---|---|---|
| 5,511,571 | A * | 4/1996 | Adrezin et al. | 135/66 |
| 5,794,639 | A * | 8/1998 | Einbinder | 135/67 |
| 5,853,219 | A * | 12/1998 | Santuccio | 297/5 |
| 6,183,425 | B1 * | 2/2001 | Whalen et al. | 600/592 |
| 6,298,314 | B1 * | 10/2001 | Blackadar et al. | 702/178 |
| 6,493,652 | B1 * | 12/2002 | Ohlenbusch et al. | 702/160 |
| 6,536,544 | B1 * | 3/2003 | Egawa et al. | 180/19.3 |
| 6,540,039 | B1 * | 4/2003 | Yu et al. | 180/253 |
| 6,611,789 | B1 * | 8/2003 | Darley | 702/160 |
| 6,644,976 | B2 * | 11/2003 | Kullok et al. | 434/236 |
| 6,645,126 | B1 * | 11/2003 | Martin et al. | 482/54 |
| 6,666,796 | B1 * | 12/2003 | MacCready, Jr. | 482/51 |
| 7,065,408 | B2 * | 6/2006 | Herman et al. | 607/49 |
| 7,190,141 | B1 * | 3/2007 | Ashrafiuon et al. | 318/568.12 |
| 7,647,196 | B2 * | 1/2010 | Kahn et al. | 702/149 |
| 2004/0102723 | A1 * | 5/2004 | Horst | 601/5 |
| 2005/0279551 | A1 | 12/2005 | LoPresti | |
| 2006/0195050 | A1 * | 8/2006 | Alwan et al. | 600/595 |
| 2006/0292533 | A1 * | 12/2006 | Selod | 434/247 |
| 2007/0233403 | A1 * | 10/2007 | Alwan et al. | 702/33 |
| 2008/0114272 | A1 * | 5/2008 | Herr et al. | 600/595 |

FOREIGN PATENT DOCUMENTS

| | | |
|---|---|---|
| WO | WO-2006014533 A2 | 2/2006 |
| WO | WO-2006014533 A3 | 2/2006 |

OTHER PUBLICATIONS

International Search Report for International Application No. PCT/US05/24072 (Apr. 28, 2006).

Sheldon, R S., "Quantification of human motion: gait analysis-benefits and limitations to its application to clinical problems", Journal of Biomechanics, vol. 37, Issue 12, (Dec. 2004), pp. 1869-1880.

Karcnik, T et al., "Using motion analysis data for foot-floor contact detection", Medical and Biological Engineering and Computing, vol. 41, No. 5, (Sep. 2003), pp. 509-512.

Fay, Brain T., et al., "The science behind mobility devices for individuals with multiple sclerosis", Medical Engineering & Physics, vol. 24, issue 6, (Jul. 2002), pp. 375-383.

"Number of Persons Using Assistive Technology by Age of Person and type of Device", National Center for Health Statistics, (1994), 4 pages.

Wasson, Glenn et al., "User Intent in a Shared Control Framework for Pedestrian Mobility Aids", IEEE International Conference on Intelligent Robots and Systems (IROS), (2003), 6 pages.

Fast, A et al., "The Instrumented Walker: Usage Patterns and Forces", Archives of Physical Medicine & Rehabilitation, vol. 76, issue 5, (May 1995), pp. 484-491.

Bachschmidt, R A., et al., "Walker-assisted gait in rehabilitation: a study of biomechanics and instrumentation", IEEE Transactions on Neural Systems and Rehabilitation Engineering, vol. 9, issue 1, (Mar. 2001), pp. 96-105.

Chen, Chia-Ling et al., "Temporal stride and force analysis of cane-assisted gait in people with hemiplegic stroke", Archives of Physical Medicine and Rehabilitation, vol. 82, Issue 1, (Jan. 2001), pp. 43-48.

Aminian, K et al., "Temporal feature estimation during walking using miniature accelerometers: an analysis of gait improvement after hip arthroplasty", Medical and Biological Engineering and Computing, vol. 37, No. 1, (Jan. 1999), pp. 686-691.

Mansfield, Avril et al., "The use of accelerometry to detect heel contact events for use as a sensor in FES assisted walking", Medical Engineering & Physics, vol. 25, Issue 10, (Dec. 2003), pp. 879-885.

Pappas, I P., et al., "A reliable gyroscope-based gait-phase detection sensor embedded in a shoe insole", IEEE Sensors Journal, vol. 4, Issue 2, (Apr. 2004), pp. 268-274.

Pappas, I P., et al., "A reliable gait phase detection system", IEEE Transactions on Neural Systems and Rehabilitation Engineering, vol. 9, Issue 2, (Jun. 2001), pp. 113-125.

Skelly, M M., et al., "Real-time gait event detection for paraplegic FES walking", IEEE Transactions on Neural Systems and Rehabilitation Engineering, vol. 9, Issue 1, (Mar. 2001), pp. 59-68.

Wasson, Glenn et al., "An Assistive Robotic Agent for Pedestrian Mobility", International Conference on Autonomous Agents, (2001), pp. 169-173.

Wasson, G et al., "Effective Shared Control in Cooperative Mobility Aids", In Proceedings of the Fourteenth international Florida Artificial intelligence Research Society Conference, (May 21-23, 2001), pp. 509-513.

* cited by examiner

INSTRUMENTED MOBILITY ASSISTANCE DEVICE

CROSS-REFERENCE TO RELATED APPLICATIONS

This application is a continuation application of, and claims priority to, International Application No.: PCT/US2005/024072, filed on Jul. 7, 2005, and titled INSTRUMENTED MOBILITY ASSISTANCE DEVICE, which itself claims priority to U.S. Provisional Application No. 60/586,107, filed Jul. 7, 2004, and titled Device for the Passive Assessment of Walker Assisted Gait Parameters. The entire contents of the above-referenced applications are incorporated by reference in their entireties.

STATEMENT OF GOVERNMENT RIGHTS

This invention was made with government support funded under the National Science Foundation (NSF Award ID 0004247). The United States government has certain rights in the invention.

TECHNICAL FIELD

This description relates to mobility-assistance devices.

BACKGROUND

Mobility-assistance devices are used to enable or enhance a mobility of one or more users. Such devices provide an amount of mobility assistance ranging from minimal assistance, such as, for example, canes or walking sticks, all the way to virtually complete assistance, such as, for example, self-powered wheel chairs. In such devices, the level of mobility assistance is often inversely proportional to a level of independence of the user, so that, for example, a user with a cane is generally able to navigate in areas that are less accessible to a user of a wheelchair.

One type of mobility assistance device is known as a walker, and is known to provide significant mobility assistance, while still allowing or requiring the user to supply meaningful effort. In this way, the user may maintain a certain level of fitness, vitality, and feeling of empowerment, any of which may otherwise be compromised if the user accepts lower levels of mobility and/or a higher degree of mobility assistance. Further, the walker may provide a good balance between a level of assistance that is required and a level of independence that is desired.

Various types of users exist who may benefit from such mobility assistance devices. For example, elderly users with limited mobility may use a walker to provide weight support, balance, or other mobility assistance. Other clinical populations, such as, for example, the injured or infirm, may benefit from such mobility assistance, as well.

SUMMARY

According to one general aspect, a method includes receiving a sensor signal from a sensor associated with a mobility-assistance device operated on a surface by a user, relating the sensor signal to a contact attribute associated with a contact of the user with the surface, and determining a gait characteristic of the user, based on the contact attribute.

Implementations may include one or more of the following features. For example, receiving the sensor signal from the sensor may include receiving the sensor signal from the sensor associated with a handle of the mobility-assistance device. Also, receiving the sensor signal from the sensor may include receiving a force signal or a moment signal associated with a force exerted by the user on the mobility assistance device.

Relating the sensor signal to a contact attribute may include relating the sensor signal to an initial foot contact of a foot of the user with the surface, or to a foot-off contact of a foot of the user from the surface. Relating the sensor signal to a contact attribute also may include correlating gait-related signal variations of the sensor signal with the contact attribute. In another implementation, relating the sensor signal to a contact attribute may include determining a peak of the sensor signal, and correlating the peak with the contact attribute.

Determining the gait characteristic of the user may include determining one or more of a group of gait characteristics that includes a gait step count, a gait pace, or timing information of different gait phases. Determining the gait characteristic of the user may include determining the gait characteristic based on a supplemental sensor signal from a supplemental sensor associated with the mobility assistance device. In this case, determining the gait characteristic of the user may include determining one or more of a group of gait characteristics that includes an instantaneous walking velocity, an average walking velocity, a step length of the user, or a stride length of the user. In another implementation, determining the gait characteristic of the user may include determining a stability measure of the mobility assistance device.

Also, a longitudinal analysis may be performed based on the gait characteristic. In this case, performing the longitudinal analysis may include collecting data associated with the gait characteristic over a time period, and performing a trend analysis on the data.

In another general aspect, a system includes a data acquisition system that is operable to receive a sensor signal from a sensor associated with a mobility assistance device, and a use analyzer that is operable to relate the sensor signal to a contact attribute associated with a contact of a user of the mobility assistance device with an underlying surface, and further operable to determine a gait characteristic of the user, based on the contact attribute.

Implementations may have one or more of the following features. For example, the sensor may include at least one of a force or moment sensor. The contact attribute may include at least one of a foot-initial contact of the user with the surface or a foot-off contact of the user from the surface. The use analyzer may be operable to relate the sensor signal to the gait characteristic by implementing a peak detection algorithm on the sensor signal.

According to another general aspect, a system includes a mobility assistance device, a sensor attached to the mobility assistance device and operable to convert an operational action of a user of the mobility assistance device into a sensor signal, and a use analyzer that is operable to relate the sensor signal to a contact attribute associated with a contact of the user of the mobility assistance device with an underlying surface, and further operable to determine a gait characteristic of the user, based on the contact attribute.

Implementations may have one or more of the following features. For example, the mobility assistance device may include a handle, and the sensor may be mounted in association with the handle. The sensor may include at least one of a force or moment sensor. The contact attribute may include at least one of a foot-initial contact of the user with the surface or a foot-off contact of the user from the surface.

According to another general aspect, a computer program product encodes a computer program for executing on a computing device a computer process. The computer process includes receiving a sensor signal from a sensor associated with a mobility-assistance device operated on a surface by a user, relating the sensor signal to a contact attribute associated with a contact of the user with the surface, and determining a gait characteristic of the user, based on the contact attribute.

Implementations may have one or more of the following features. For example, the sensor may include at least one of a force or moment sensor. The contact attribute may include at least one of a foot-initial contact of the user with the surface or a foot-off contact of the user from the surface.

According to another general aspect, a method includes receiving a sensor signal from a sensor associated with a mobility-assistance device operated by a user, determining a plurality of tip-over axes defined with respect to a frame of the mobility-assistance device, and determining a stability measure of the mobility-assistance device, based on the sensor signal and the tip-over axes.

Implementations may have one or more of the following features. For example, receiving the sensor signal from the sensor may include receiving a moment or a force signal associated with a force exerted by the user on the mobility assistance device.

Determining the plurality of tip-over axes with respect to the frame may include determining the tip-over axes with respect to ground contact points of the frame with a surface underlying the mobility-assistance device. Determining the plurality of tip-over axes with respect to the frame may include relating the sensor signal to the tip-over axes using a rigid body model associated with the frame.

Determining the stability measure of the mobility-assistance device may include determining a force-angle measurement about at least one of the tip-over axes. Determining the stability measure of the mobility-assistance device may include determining a resultant force on a center of mass of the mobility-assistance device. In this case, determining the stability measure of the mobility-assistance device may include determining components of the resultant force, determining an angle that at least one of the components makes about each of the tip-over axes, with respect to the normal to the corresponding one of each respective tip-over axis, and determining the stability measure based on the angle force product.

Determining the stability measure of the mobility-assistance device also may include determining a first stability margin associated with a first tip-over axis and a second stability margin associated with a second tip-over axis of the tip-over axes, and determining the stability measure based on the first stability margin and the second stability margin. Determining the stability measure of the mobility-assistance device may include determining a ground reaction force at each of a plurality of contact points of the frame with an underlying ground surface, and determining the stability measure based on a minimum ground reaction force detected at one of the contact points.

Also, a user stability of the user may be inferred, based on the stability measure.

According to another general aspect, a system includes a data acquisition system that is operable to receive a sensor signal from a sensor associated with a mobility assistance device, and a use analyzer that is operable to relate the sensor signal to a rigid body model associated with a frame of the mobility assistance device, and further operable to determine a stability measure associated with the mobility assistance device, based on the sensor signal and the rigid body model.

Implementations may have one or more of the following features. For example, the sensor may include a force sensor or a moment sensor.

The use analyzer may be operable to determine a plurality of tip-over axes defined with respect to the frame of the mobility-assistance device, and to determine the stability measure based on the tip-over axes. The use analyzer may be operable to determining a force-angle measurement about at least one of the tip-over axes, and to determine the stability measure based on the force-angle measurement. The use analyzer may be operable to determine a ground reaction force at a contact point of the frame of the mobility assistance device with an underlying ground surface, and to determine the stability measure based on the ground reaction force.

The details of one or more implementations are set forth in the accompanying drawings and the description below. Other features will be apparent from the description and drawings, and from the claims.

DETAILED DESCRIPTION

Figure 1:
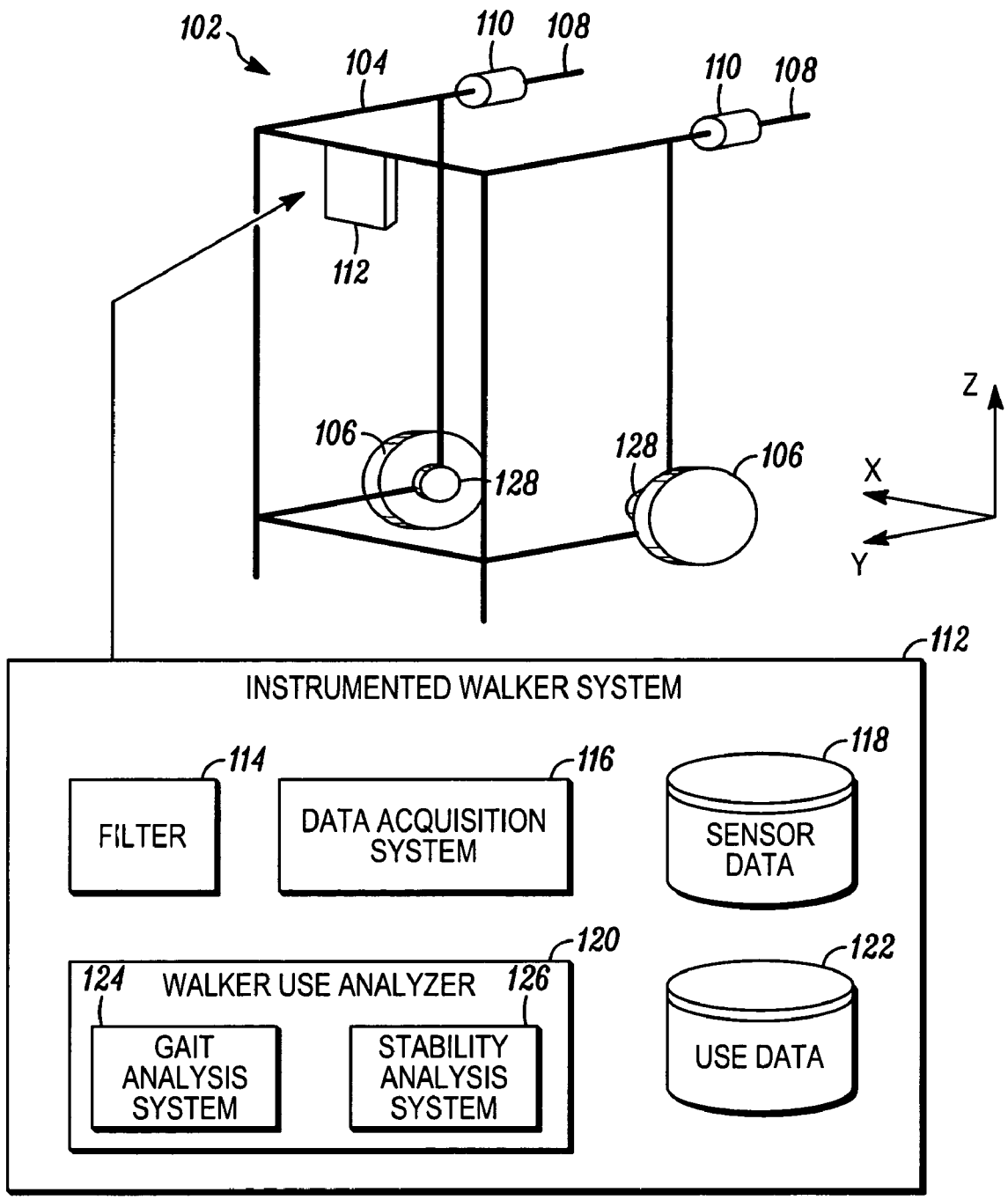
FIG. 1 is a block diagram of an instrumented mobility assistance system.

FIG. 1 is a block diagram of an instrumented mobility assistance system 100. In FIG. 1, a walker 102 is illustrated as an example of a mobility assistance device. The walker 102 includes a frame 104 and wheels 106. The walker 102 provides support and balance to a user (not illustrated) who grasps handles 108 of the walker 102. As a result, a mobility and independence of the user may be enhanced.

Also in FIG. 1, sensors 110 are disposed within, coupled to, or are otherwise associated with, the handles 108, as one example of possible deployment on the frame 104. In some implementations, the sensors 110 may include force and/or moment sensors. The sensors 110 act as transducers that are operable to translate information regarding an action of the user with respect to the walker 102 into an electrical signal(s) that is received at an instrumented walker system 112.

The instrumented walker system 112 analyzes the signals from the sensors 110 to characterize a use of the walker 102 by the user. In this way, the instrumented walker system 112 may characterize the use of the walker 102, so as, for example, to determine or improve an effectiveness of the walker 102 with respect to the particular user, or with respect to all users. In other examples, the system 112 may be used to assist in monitoring, diagnosing, treating, or rehabilitating the user.

In some implementations, the sensors 110 include force and/or moment sensors. For example, the sensors 110 may include load cells that are operable to convert a force and/or weight of the user into an electrical signal for input into the system 112. Such load cells may include, for example, a strain gage that is operable to change an internal resistance when stressed, in proportion to the stress. A corresponding electrical signal may be derived from this phenomenon, and may then be amplified, filtered, or otherwise manipulated for analysis.

Such load cells or other types of the sensors 110 may thus be used to determine force components exerted on the handles 108, and/or on the walker 102 as a whole, by the user. As the user moves with the assistance of the walker 102, such force components may be exerted in any of the x, y, or z directions illustrated by the coordinate system of FIG. 1.

Additionally, or alternatively, the sensors 110 may be used to determine moment measurements, which generally refer to a product of a quantity (e.g., a force) and a distance (or some power of the distance) to some point associated with that quantity. For example, the term torque (tendency to turn about a point or axis) refers to the moment of force, so that, for example, if a force exerted by the user tends to rotate one of the handles 108 about some point, then the moment, or turning effect, is the product of the force and the distance from the point to the direction of the force. In the case of the walker 102, then, it may be seen that forces exerted by the user may create, for example, moments of force about the handles 108 (or, more generally, about any of the x, y, or z axes), which may be detected by the sensors 110.

The instrumented walker system 112 receives resulting signals from the sensors 110, and, if necessary, amplifies and/or filters the signals at a filter 114. A data acquisition system 116 then collects the (possibly filtered) data, which may include measurements over time of forces and moments with respect to any of the x, y, and z axes, and from either or both of the sensors 110 on the handles 108. This sensor data may be stored in a memory 118, and/or may be provided to a walker use analyzer 120.

The walker use analyzer 120 analyzes the sensor data in order to characterize a use of the walker 102 by the user. That is, as described in more detail below, the walker use analyzer 120 may characterize, for example, actions of the particular user, actions of general users or classes of users, a reaction of the walker 102 to the user(s) in question, or a reaction of the user and/or the walker 102 in specific contexts (e.g., sharp turns). The resulting use data may then be stored in a memory 122.

In some implementations, for example, the walker use analyzer 120 inputs the sensor data into a gait analysis system 124. The gait analysis system 124 is operable to determine, as discussed in more detail below, characteristics of a gait of the user, including, for example, a step count of the user and/or pace information.

In the same or other implementations, the sensor data may be received at a stability analysis system 126, which is operable to determine a stability of the walker 102. As is also described in more detail below, stability may be characterized in a number of different manners, and may be useful, for example, in determining a tip-over point of the walker 102, perhaps with respect to the particular user, or more generally, or with respect to a particular terrain or usage experienced by the walker 102.

Finally in FIG. 1, additional sensors 128 are illustrated in conjunction with the wheels 106, and may include, for example, velocity and/or distance sensors. For example, the sensors 128 may include odometers that are operable to measure a distance traveled by the user with the walker 102.

As the sensors 128 also may be in communication with the system 112, data from the sensors 128 may be used to determine additional information regarding a use of the walker 102 by the user. For example, as described in more detail below, the gait analysis system 124 may use the sensor data (including data from the sensors 110 and the sensors 128) to determine an average or instantaneous velocity of the user, as well as a step length and/or stride length of the user.

In the system 100, then, use of sensor data, such as, for example, measured forces and moments, may be used to passively derive basic gait characteristics and other use information related to the walker 102. Thus, wheeled walkers may easily be augmented with simple and relatively low-cost instrumentation technologies to provide a wide range of functionality and gait characteristics. In addition, this information may be used for maximizing user stability, determining control actions in controlled walkers (discussed in more detail below), and various other advantages that benefit users of the walker 102.

As should be apparent, the system 100 allows walker use information to be obtained, stored, and analyzed in situ, in every-day environments experienced by walkers and their users. As a result, user and/or walker assessments may be more meaningful and useful. Additionally, accurate and timely monitoring of the walker and/or user may be performed, in order, for example, to ensure a safety of the user or to monitor efficacy of medical interventions, such rehabilitation intervention, to enhance their benefit to the user.

In particular, longitudinal assessment of functionality of the user, both inside and outside the home, may be used to provide clinicians with continuous measures of the user's functional ability and activity levels, and may hence help evaluate the user's health over a long period of time. Moreover, functional assessment in the user's natural environment, e.g., outside a clinic or gait lab, may be useful for monitoring the effectiveness of therapeutic interventions, including surgeries, drug therapy, or physical therapy, over extended periods of time.

For example, in performing longitudinal assessments, data may be collected over a period of time, for use in performing a trend analysis. For example, if data streams regarding step count, pace, timing of gait phases, instantaneous or average walking velocity, step length, stride length, or stability are collected over time, then trend analysis on one or more of these types of data, or in combinations thereof, may be informative to clinicians on the efficacy, or lack thereof, of interventions such as physical exercise or therapy, walking, rehabilitation, or medication. Additionally, for example, if data streams regarding any of the gait characteristics collected by the device longitudinally are collected over time, then trend analysis may demonstrate a sudden or abrupt change in one or more of these types of data, or in combinations thereof. Such a trend change may demonstrate, by itself, meaningful information related to a condition of the user, including, for example, a possible onset of a particular disease or condition, or a development of a disease or condition to acute status. Similarly, trend analysis may indicate a sudden failure of a joint or bone of the user. Further, use of the trend analysis information may be used in conjunction with other types of analyses in order to monitor or evaluate the user and/or the walker.

In the example of FIG. 1, the instrumented walker system 112 is illustrated as being on-board the walker 102. However, in other implementations, the system 112 may be implemented in whole or in part apart from the walker 102. For example, in some implementations, data acquisition may occur at the walker 102, and then may be stored (for later downloading) or transmitted for subsequent processing. In other implementations, sensor data may be transmitted directly from the sensors 110 and/or 128 to a remote version of the system 112.

As should be understood, such downloading and/or transmission of data may occur by way of wireless or wired communications. For example, the sensor data 118 may be stored locally to the walker 112 throughout some period of time, and thereafter may be connected to a computer for downloading over a wired or wireless connection including, by way of example and not limitation, Radio Frequency, Bluetooth, Infrared, optical communications, or other communications techniques. In other examples, the sensor data 118 may be collected and transmitted to a portable computing device (e.g., a personal digital assistant (PDA)) of the user, at which other components of the system 112 may be implemented.

In the implementations described above, the sensors 110 are disposed only on or in the handles 108 of the walker 102. As a result, it is not necessary to dispose other sensors or information-tracking devices on a person of the user. Nonetheless, in some implementations, additional use information may be detected or determined based on sensors that are disposed on a person or clothing of the user.

Additionally, the sensors 110 need not be disposed in association with the handles 108, and may be disposed in association with other portions of the walker 102, including, for example, in association with the frame 104 and/or the wheels 106, or in association with some combination of the handles 108 (or just one of the handles 108), the frame 104, and the wheel(s) 106. Further, the sensors 110 are described as force/moment sensors, e.g., load cells, but it should be understood that various types of these sensors, and other sensors, not specifically mentioned here, also may be used. For example, other sensor types that may be used include piezoelectric films, capacitive force sensors, or pressure sensors.

Figure 2:
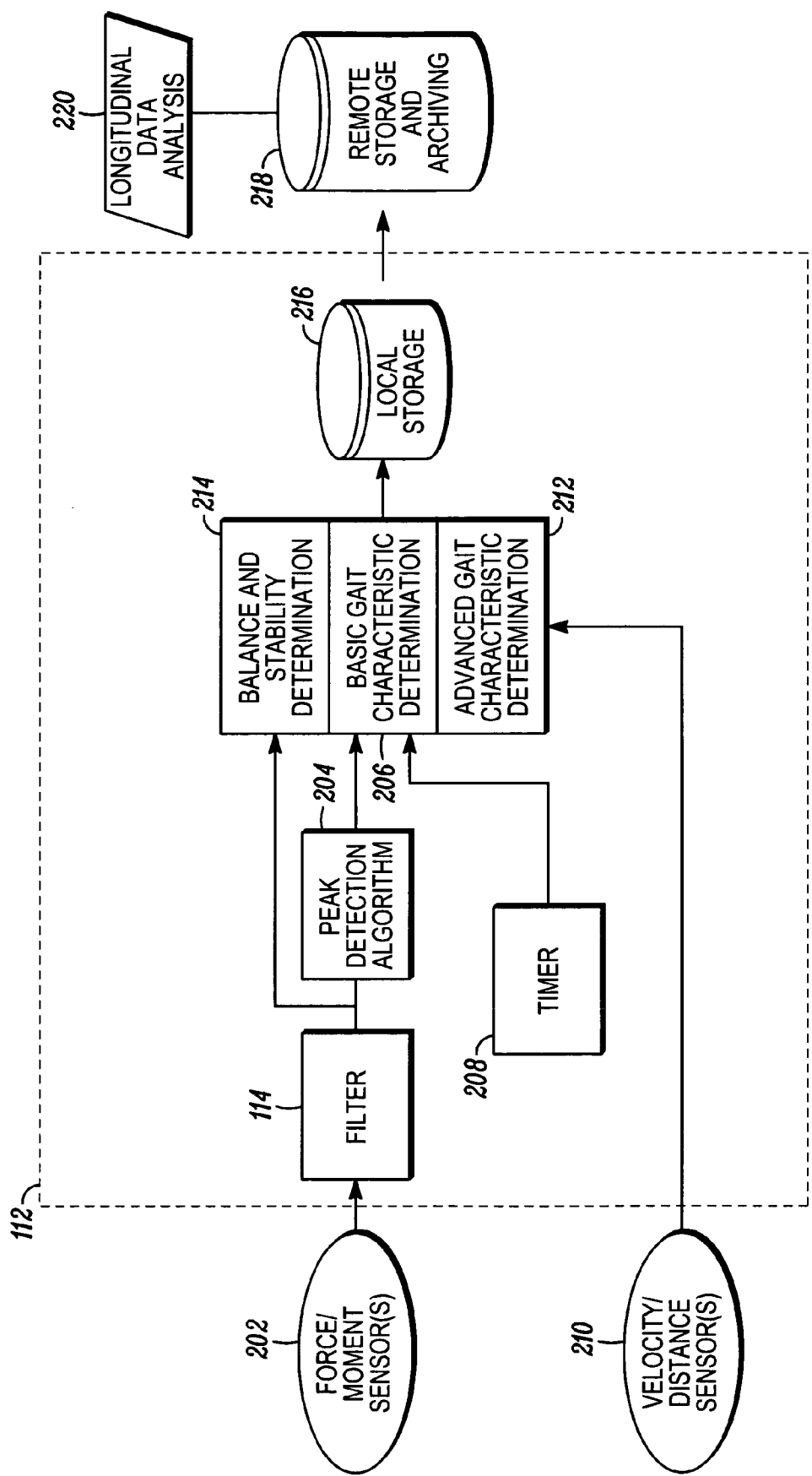
FIG. 2 is a block diagram of an instrumented walker system of FIG. 1.

FIG. 2 is a block diagram of the instrumented walker system 112 of FIG. 1. In FIG. 2, force/moment sensor(s) 202 are specific examples of the sensors 110 described above. Accordingly, force and/or moment data from the sensors 202 is received at the filter 114.

For example, a maximally flat response Infinite Impulse Response (IIR) low-pass filtering algorithm with a cut-off frequency of 3 Hz may be used in the data processing. In some implementations, in order to eliminate the phase shift caused by filtering, a non-causal bi-directional filter may be used. Such a filter may perform zero-phase shift digital filtering by processing the input data in both the forward and reverse directions. In other implementations, a causal filter with minimal phase shift may be used, or a causal filter with a linear phase response with a minimal order necessary to guarantee a desired on-line processing speed may be used.

Other filter types, whether implemented in software or hardware, also may be used. For example, Finite Impulse Response (FIR) filters or Butterworth IIR filter may be used. A magnitude response of the Butterworth IIR filter may be designed to be flat, and the phase response may be designed to be approximately linear in the pass-band. With these characteristics and lower order than the corresponding FIR filter, a high order Butterworth filter may be implemented for on-line gait detection. A minimum phase shift Butterworth IIR filter for on-line gait characterization also may be used.

Once filtered, the force/moment sensor data may be analyzed, and characteristics of the data may be correlated with aspects of the user's motion. For example, forces and moments recorded from the handle(s) 108 may include cyclic or quasi-cyclic changes reflecting a gait cycle of the user, and, from such changes, gait characteristic(s) may be determined.

In particular, in the example of FIG. 2, and as explained in more detail below, a peak (or valley) of a particular force or moment component(s) may be associated with a gait characteristic of the user, and, in particular, may be associated with a contact attribute associated with a contact of the user with a (e.g., ground) surface that is supporting the user and the walker 102.

Consequently, in the example of FIG. 2, a peak detection algorithm 204 may be implemented to determine such peaks, and these peaks may be correlated with contact attributes, such as, for example, an initial foot contact of the user with the ground surface, or a foot-off (i.e., dis-engagement of contact) of the user from the ground surface. Initial foot contact may include a heel-strike, or a toe-strike, or, in the case of a flat-footed user, may include a middle, majority, or entirety of the user's foot contacting the surface. Similarly, foot-off events may include a toe-off, heel-off, or middle/entire foot-off from the ground surface. Of course, in cases where the user requires a prosthesis of some sort, there may not be foot contact per se, and so the term contact attribute is intended to include any engaging, maintaining, or dis-engaging of contact of the user, or a portion of the user, or a prosthesis of the user, with the supporting surface.

The determination of the contact attributes allow for determination of what are termed herein as "basic" gait characteristics, and which include, for example, step count and/or pace information. Timing information from a timer 208 may be used in conjunction with the peak detection algorithm 204 to determine the basic gait characteristics 206, such as pace (or number of steps per minute).

As referenced above, additional information from velocity/distance sensor(s) 210, which represent specific examples of the sensors 128, may be used in conjunction with the basic gait characteristic determination 206, in order to perform an advanced gait characteristic determination 212. The advanced gait characteristic determination 212 may include, for example, a determination of an instantaneous or average walking velocity of the user, a step length of the user, or a stride length of the user.

Additionally, or alternatively, a balance and stability determination 214 may be made. For example, forces and moments applied to the walker 102 in the vertical direction and measured at the handles 108 may be used to measure ground reaction forces at the wheels 106, using standard rigid body transformations, such as, for example, Walker's rigid body model. As a result, for example, the ground reaction forces may be used to assess an index of stability of the walker/user system, throughout a plurality of gait phases and navigational modes. In this way, for example, a tip-over point or propensity of the walker 102 may be determined, and a safety and mobility of the user may be judged and may consequently be enhanced.

In the implementation of FIG. 2, local storage 216 is used to store the sensor data and/or gait and stability determinations. Contents of the local storage 216 may then be transferred to a remote storage and archiving memory 218, for performance of a longitudinal data analysis 220.

Figure 3:
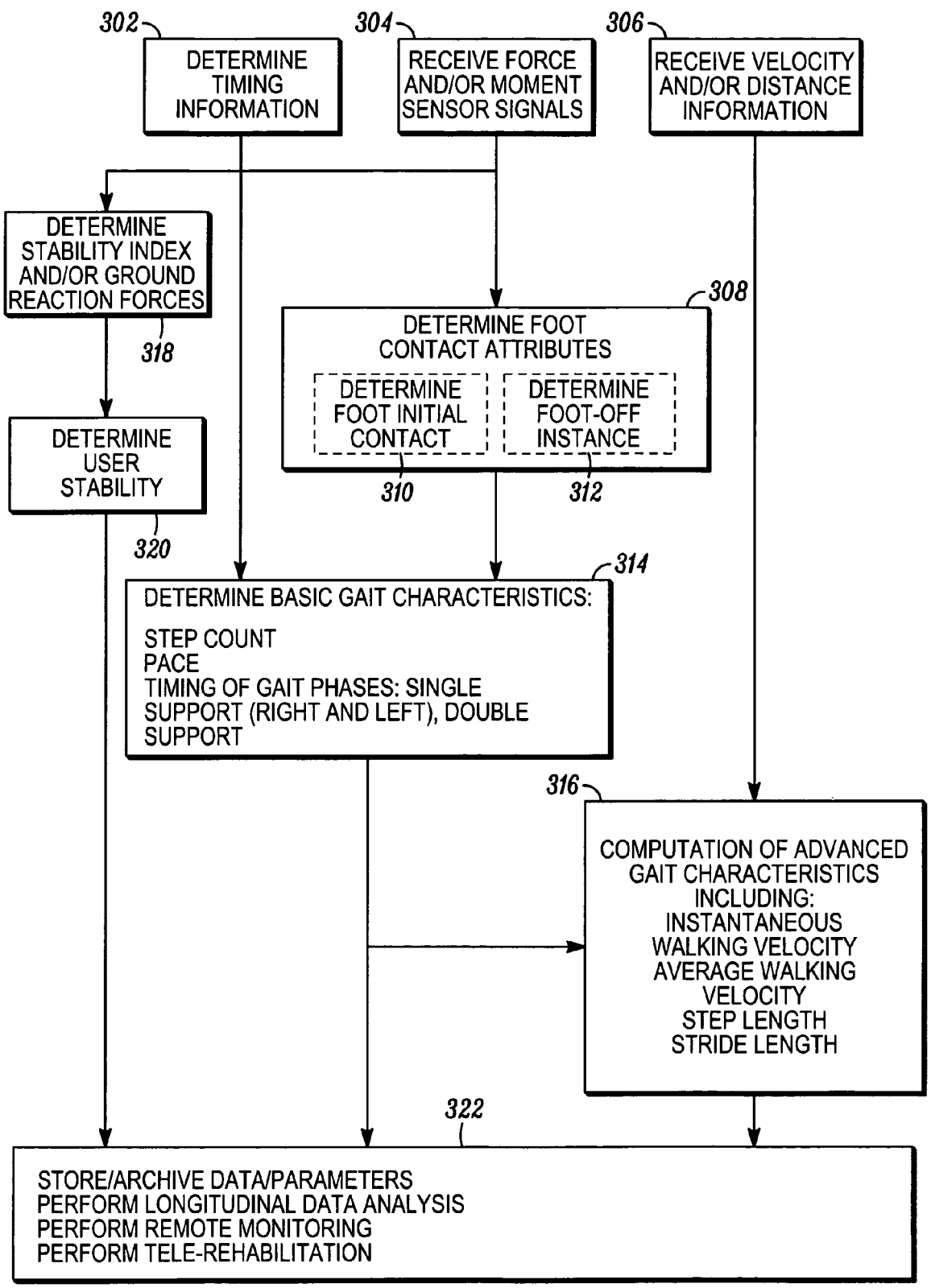
FIG. 3 is a flowchart illustrating example operations of the systems of FIGS. 1 and 2.

FIG. 3 is a flowchart 300 illustrating example operations of the systems of FIGS. 1 and 2. In FIG. 3, timing information is determined (302) to assist in the analysis of the use of the walker 102. For example, the time 208 of FIG. 2 may be continually running, or may be initiated when data is to be collected, in order to provide reference points for calculations of the quantities discussed below.

Force and/or moment signals are received from the sensor signals 110 (304). In one implementation, for example, forces and moments applied to the handle(s) 108 are measured via two commercially-available 6-degree of freedom (DoF) load cells. As described above, such sensors may be used to provide the load/moment transfers between the walker 102 and the user. At a same time, or later, velocity/distance and/or other information may be received from the additional sensors 128 (306).

Information regarding the gait of the user may be contained in all of the force moment components detected by the sensors 110 to one degree or another. In some implementations, this gait information is derived primarily or exclusively from the moment resulting from the user pushing down on the handle(s) 108. In this way, a single axis sensor on each of the handles 108 may be sufficient to measure gait-related signal variations, such as, for example, the gait-related signal variations discussed below.

For example, as referenced above with respect to FIG. 2, peaks in the sensor signals from sensors 110 are examples of such gait-related signal variations, and, in particular, may be correlated with contact attributes related to a contact of the user with an underlying ground surface during normal use of the walker 102. As already discussed, since such contact attributes refer to contact between a foot (or other feature, e.g., prosthesis) of the user and the underlying surface, the contact attributes may include (and be referred to as) foot contact attributes or surface contact attributes.

Thus, by analyzing gait-related signal variations, such as detected signal peaks, foot contact attributes may be determined (308). One example of determining foot contact attributes include determining foot initial contacts (310), e.g., heel strikes corresponding to an initial contacting of the user's foot with the ground during a stride. A second example includes determining foot-off instances (312), such as toe-off instances corresponding to a final contacting of the user's foot with the ground during a stride.

For example, in performing heel strike detection, a correlation may exist both between forces in the direction normal to the ground, $F_Z$, and a corresponding moment around the (x) axis that is parallel to the ground and perpendicular to the direction of travel, i.e., the $M_X$ moment (or between other detected forces or moments). That is, peaks in either of the two signals $F_Z$ and $M_X$ may be shown to coincide with the heel strike instance(s).

Figure 4A:
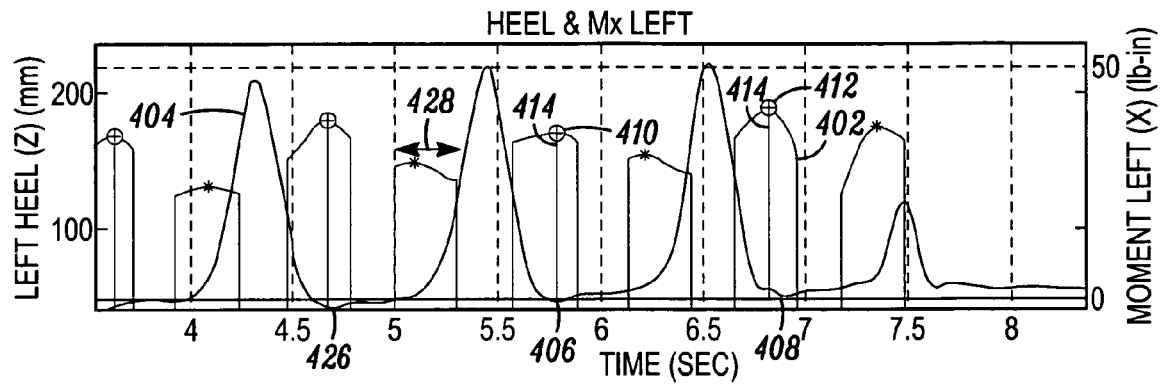
FIGS. 4A and 4B are graphs illustrating a correlation of a sensor signal with foot-strike instances of a user of the instrumented mobility assistance device of FIG. 1.
Figure 4B:
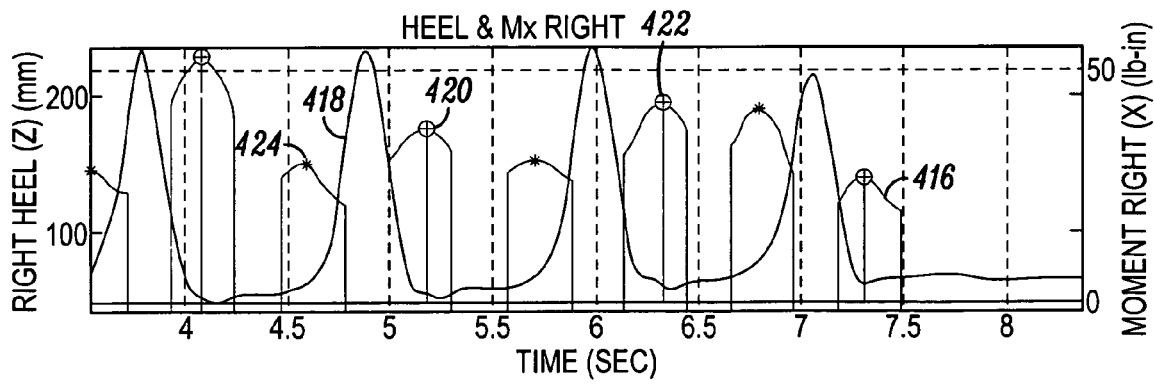

FIGS. 4A and 4B illustrate graphs showing a correlation between sensor signal peaks and heel strike instances. In particular, FIG. 4A illustrates a graph of the moment $M_X$ signal 402 for a left foot of the user.

The signal 402 is illustrated against a reference signal 404 that illustrates a known occurrence of heel strike instances. In the example of FIG. 4, the reference signal 404 illustrates motion data collected by a known vision-based motion capture system in which a motion model (walker/user) is computed in a conventional manner, using reflective markers attached to various points on the user's body and on the walker frame 104, which are detected by six 120 Hz video cameras. This motion capture system is operable to create a 3-D motion model by using the positions in the (x-y-z) space of the particular real points (markers) placed on the user and on the walker frame 104.

In FIG. 4, then, the reference signal 404 illustrates a known representation of heel initial contacts as determined by the motion capture system, in which the heel initial contacts may be identified as valleys (e.g., valleys 406 and 408) in the vertical component of the trajectory traces of markers attached to the heel(s) of the user. Thus, for example, points 410 and 412 illustrate heel initial contacts correlate with peaks of the $M_X$ moment signal 402. The accuracy of these peaks in determining heel initial contacts may thus be determined by comparison against the known instances of heel initial contacts associated with valleys of the reference signal 404, which, as shown by reference lines 414, align favorably.

The peak 412 of the left $M_X$ signal 402, it may be noted, has higher amplitude than the peak 410, and coincides with heel initial contact of the corresponding (i.e., left) foot. In contrast, the peak 410 of the left $M_X$ signal 402 is lower in amplitude than the peak 412, and corresponds to heel initial contact of the opposite (i.e., right) foot. Accordingly, as may be seen in FIG. 4A, such higher and lower peaks alternate repetitively.

Similar comments apply to FIG. 4B, in which a right moment $M_X$ signal 416 is compared against a reference signal 418, and illustrates peaks 420 and 422 corresponding to heel initial contacts. Again, the higher peak 422 coincides with the heel initial contact of the corresponding (i.e., right) foot, while the lower peak 420 coincides with the heel initial contact of the opposite (i.e., left) foot.

This pattern reflects the lateral sway motion of the upper body of the user during ambulation, which can be modeled as an inverted pendulum, and the associated pattern of loading exerted on the walker frame. The load is transmitted through the walker's rigid frame and may be measured by ground reaction forces, as discussed in more detail, below.

This pattern in the force-moment signals was exploited in developing a peak detection algorithm to identify right and left heel initial contacts from the right and left $M_X$ signals 416 and 402, respectively. This peak detection algorithm is described in more detail below, with respect to FIG. 7.

In short, as shown in FIGS. 4A and 4B, peaks (e.g., the peak 410) in $M_X$ signals (e.g., the left $M_X$ signal 402) coincide with heel initial contacts or valleys (e.g., the valley 406) obtained from the vertical signal(s) associated with the heel marker(s) of the referenced motion capture system. In the left moment $M_X$ signal 402, then, peaks marked by circles in FIGS. 4A and 4B (e.g., the peaks 410 and 412) coincide with valleys in the corresponding heel marker signal 404, as shown. Peaks (e.g., a peak 424) in the right moment $M_X$ signal 416 marked by a "+" coincides with valleys (e.g., a valley 426) in the opposite (left) heel marker signal.

Figure 5A:
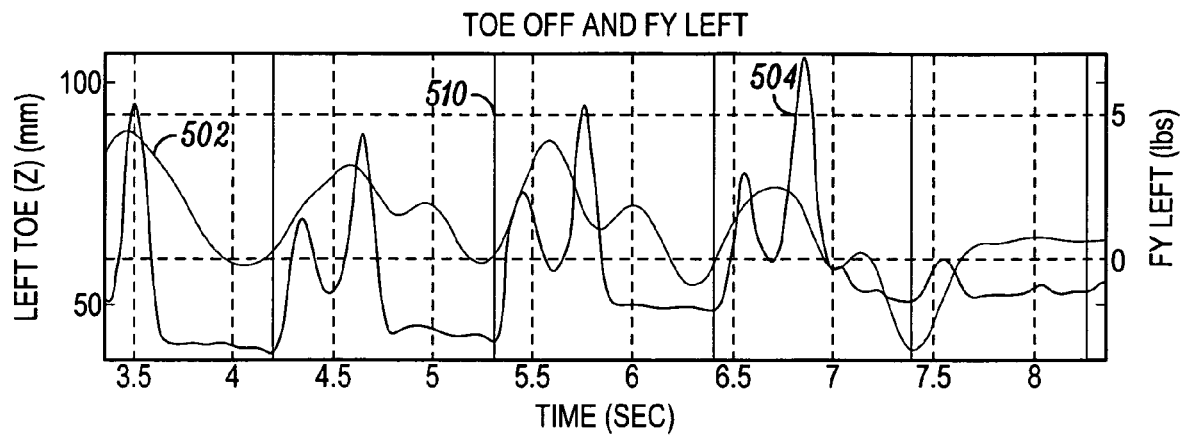
FIGS. 5A and 5B are graphs illustrating a correlation of a sensor signal with foot-off instances of a user of the instrumented mobility assistance device of FIG. 1.
Figure 5B:
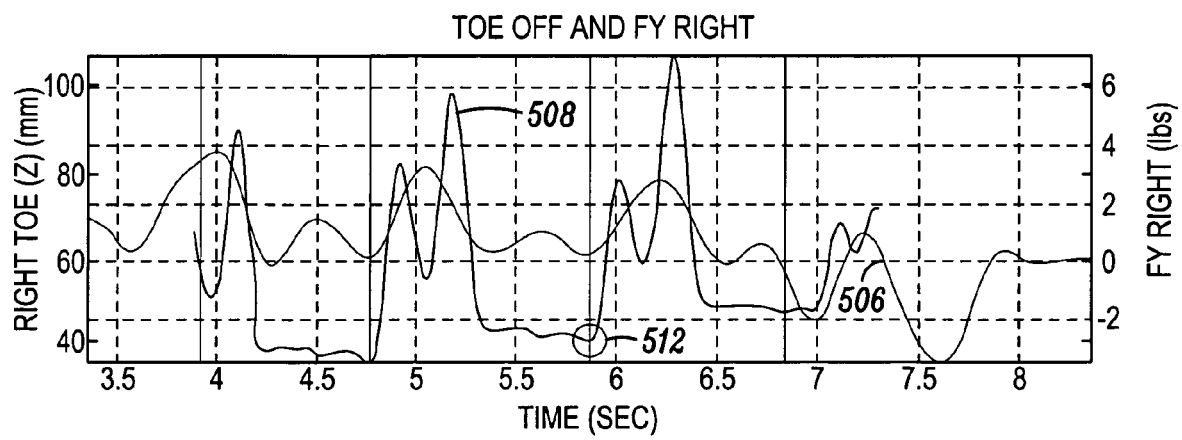

Having illustrated the determining of foot initial contact (310) of FIG. 3 by way of FIGS. 4A and 4B, the determining of foot-off instances (312) may be illustrated by the example of FIGS. 5A and 5B, in which graphs illustrating correlations between the sensor signals 110 and the foot-off instances. For example, in FIG. 5A, a correlation exists between the forward propulsion forces applied by the user, $F_Y$ (represented by a signal 502), and the toe-off event from the toe markers data captured by the reference motion capture system (represented by a reference signal 504). For example, for some users, toe-off events may coincide with the start of an appreciable increase in the forward pushing force on the handle corresponding to the foot lifting off. Similar comments may apply to a force $F_Y$ signal 506 for the right foot, with respect to a right reference signal 508.

As an alternative to a specific toe-off detection algorithm, toe-off times may be estimated using a 60% rule, based on the detected heel strike events discussed above. For example, two successive heel strikes, measured for the same foot, may be used to compute the stride time (i.e., the duration of the gait cycle) of the user. Using a known normalized gait diagram, an estimate of the toe-off event may be obtained by adding 60% of the stride time to the time of the first detected heel contact. By repeating this process, a good estimate of all subsequent toe-off events may be obtained. FIGS. 5A and 5B graphically presents the results of toe-off estimation using the 60% estimation rule mentioned above, illustrated at reference points 510 and 512.

The 60% rule of the gait for toe-off estimation may be particularly useful for a normal gait of able-bodied subjects on level grounds. However, for patient populations with abnormal gait pathologies, or for inclined ramps, this value may not be applicable. Nonetheless, the estimation method may be adapted, by changing the percentage value, to cater for these situations. Additionally, a combination of the estimation rule and the above described valley detection algorithm may be used to detect foot-off more accurately in user's with gait abnormalities or locomotor disabilities.

Returning again to FIG. 3, the determined foot contact attributes, perhaps in conjunction with determined time information, may be used to determine basic gait characteristics (314). Examples include pace/stride time/gait cycle, right and left single support phases, double support phases, and step count. Calculation of these quantities may be performed according to known methods, once the timing information and foot contact attributes are determined.

It should be noted that there is a general trend in an error of heel strikes detection, toe-off time estimation, and in the computation of the stride time, as well as the times of the single and double support phases, that increases with the turn being made. This is expected since the force-moment patterns exerted on the walker's handles 108 differ during turns, and include a component reflecting the desired direction, in addition to any support needs during the turns, with the cyclic undulations reflecting the gait cycle and its different phases.

Thus, for example, a portion of the gait cycle that the user is currently in may be determined, and, therefore, appropriate control actions may be taken with respect to, for example, a control system that may be in place for controlling the walker 102. Such a control system may enable, for example, a human/machine shared-control system that assists users by increasing the safety and speed of their daily travel. In such systems, for example, on-line gait characteristics detection may be used to determine the double support phase of the gait, and/or to initiate the control at the beginning of the double support phase for maximum dynamic stability. To the extent that the on-line detection and analysis includes errors, a measure of confidence may be ascribed to the gait information, and utilized during a decision making process for the on-line control of the walker 102 in such systems.

Further with regard to FIG. 3, and as described above, the reception of the additional sensor information, such as the determined velocity and/or distance information (306), may allow for computation of advanced gait characteristics (316). Such characteristics include, for example, an instantaneous or average walking velocity, a step length of the user, or a stride length of the user. These and other quantities may be calculated using known calculation techniques. Examples of additional sensors that may be used include incremental wheel encoders, tachometers, or odometers.

Also in FIG. 3, the determined force and/or moment signals may be used to determine a stability index and/or ground reaction forces associated with an in situ use of the walker 102 (318). From these determinations, an in situ stability of the user may be determined (320).

For example, known rigid body models may be applied to the frame 104 of the walker 102, in order to translate the forces/moments applied by the user at the handles 108 into a representation of a stability index of the walker. A stability index may be formulated for a particular walker over a plurality of navigational scenarios, such as, for example, during straight-line operation, during gradual or sharp turns of the walker 102, or over uneven surfaces.

A stability computation model may be determined, based on a force-angle stability measure associated with the forces and moments detected at the handles 108 by the sensors 110. Such a force-angle stability measure may be useful in measuring a stability of the walker 102, due to a sensitivity of the measure with respect to angular loads (e.g., external forces and moments applied by the user). The measure may be used to determine an on-line, essentially instantaneous, stability margin during navigation with the walker 102. Examples of determinations of stability measures are discussed in more detail below with respect to FIG. 7.

By determining the various gait characteristics described above, including a stability measure, the instrumented walker 102 may be used to assist in clinical gait analysis (322). In particular, the walker 102 and associated system 112 may be used to store or archive the various gait characteristics, for future analysis thereof. Additionally, since the walker 102 may be implemented as small and portable, gait analyses may be performed longitudinally "in the field," where data may be most meaningful to the use and enjoyment of the user with respect to the walker 102. Remote monitoring of the user may be performed, in order, for example, to provide care at a distance for the user, including diagnosis or re-habilitation.

Figure 6:
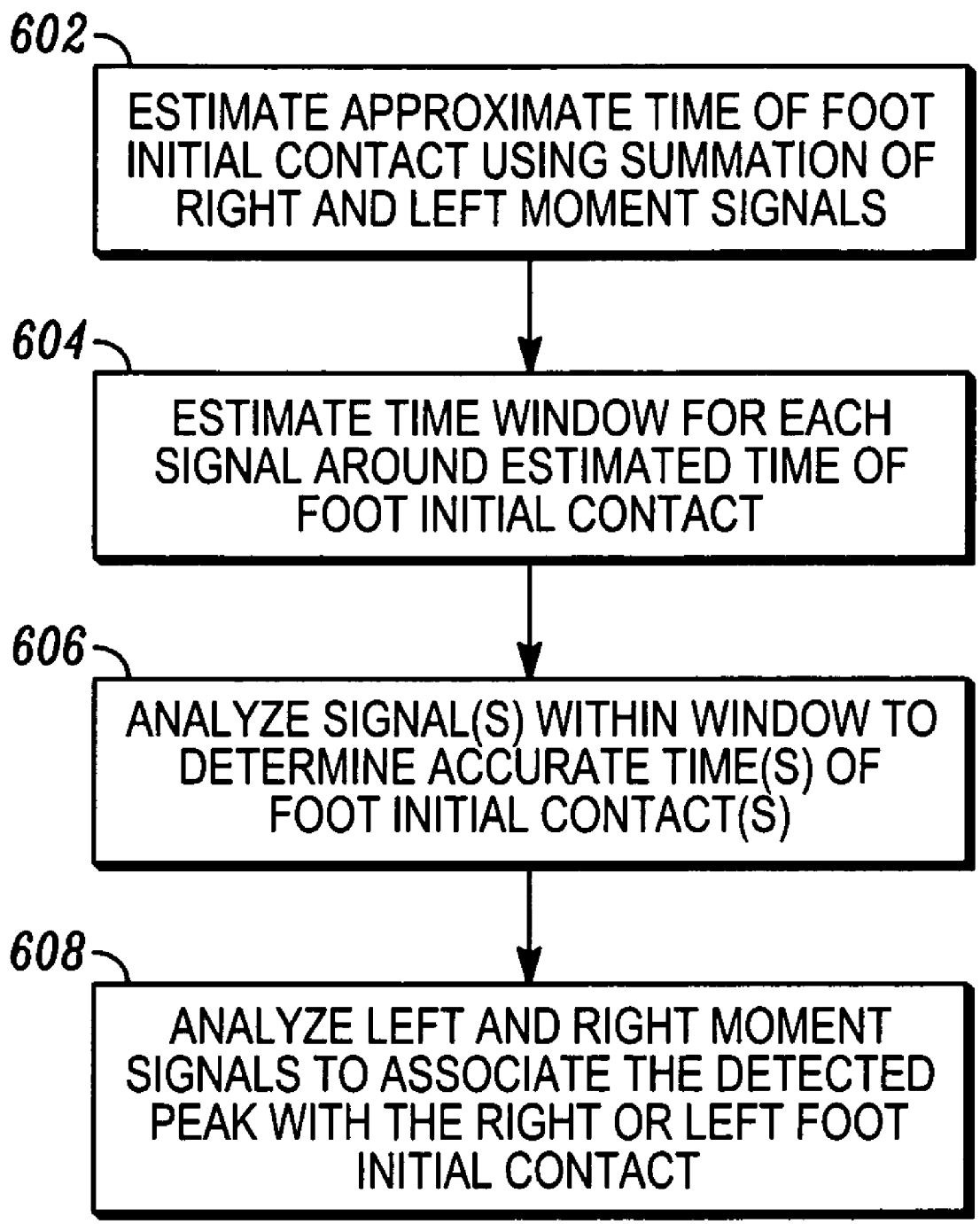
FIG. 6 is a flowchart illustrating an example of a peak detection algorithm described in conjunction with FIGS. 2-5.

FIG. 6 is a flowchart 600 illustrating an example of the peak detection algorithm described in conjunction with FIGS. 2-5, that may be used to determine heel strike instances. In FIG. 6, data from the right and left $M_X$ signals are analyzed to estimate an approximate time of each heel initial contact (602). In some implementations, the peak detection algorithm may be applied to a signal representing the summation of the right and left moment signals around the X axis (i.e., $M_{x,left}$+$M_{x,right}$). In these cases, peaks corresponding to heel initial contacts may be enhanced because they are present in each of the two signals, unlike spurious peaks, which could be due to noise.

The second step of the algorithm detects the actual timing of the heel initial contacts by analyzing the signal $M_{x,left}$ and $M_{x,right}$ independently. Specifically, the estimated heel initial contact time is used to establish a relatively narrow time window (shown as a window 428 in FIG. 4) centered at the estimated heel initial contact times (604). A size of the window 428 may be determined by an optimizing algorithm on data from randomly selected subjects, where such an optimization may be based on selecting a window width that does not miss any heel initial contact in any trial performed by the subject(s). Accordingly, a minimum window width for all subjects may be selected such that an error between the time of heel initial contacts detected by the peak detection algorithm and the heel initial contact times provided by human detection on data from the motion capture system is minimized.

The peak detection algorithm analyzes the signal in these windows to compute the accurate heel initial contact instances (606). This window method allows accurate identification of heel initial contacts (i.e. minimizes the absolute error between actual heel initial contacts and peaks identified in the moment signal), but may result in missing some peaks in each signal.

The left and right moment signals $M_X$ may then be analyzed to associate the detected peak with the right or left heel initial contact (608). For example, the peak detection algorithm may scan the $M_X$ data recorded for an entire trial in order to find a highest peak. Once this peak is detected, the algorithm may iteratively search for remaining peaks (after skipping a portion of the data that reflect a pre-determined dead-time, in order to avoid a detection of false peaks in the undulating $M_X$ signal that do not coincide with heel initial contacts). The algorithm stops when the amplitude of the current peak in sum of moments ($M_{x,left}$+$M_{x,right}$) signal falls under some threshold, such as, for example, a threshold of 10 lb-in. This technique also may be used alone, as an off-line technique for analyzing sensors signals collected at the system 112 and downloaded for later analysis.

Of course, other peak detection algorithms, or modification of the above-described algorithm, also may be used. For example, a peak detection algorithm may be used in which a step lengths history (computed from previous heel initial contacts instances) is used to adapt the width of the window for each subject and for each estimated initial contact times.

A similar data history based approach could be adopted to adapt the toe-off estimation method. The history-based peak detection and toe-off estimation algorithms may allow the adaptation of the method to cater for abnormal gait pathologies and locomotion disabilities.

The error of heel initial contact detection, toe-off time estimation, and the computed stride time, as well as the times of the single and double support phases, generally tend to increase when the user changes direction. This increase in error may be expected, since the forces and moments exerted on the handles 108 include a component reflecting the user's desire to change the direction of the walker 102, in addition to a component reflecting the user's increased need for support while performing a turn. Nevertheless, if gait characterization is limited to data collected during straight line segments (e.g., through tracking the orientation of the steering wheel using an encoder), the errors may be reduced, as may be a standard deviation of the errors.

An accuracy of the heel initial contact detection algorithm(s) described above may be established on a step-by-step basis, through comparison to the count of steps detected by a human observer inspecting the heel marker signals from the motion capture system. For example, heel initial contacts detected by the algorithm and observed on the heel marker signals within the same step time window may be scored as a hit or a true positive. If the algorithm did not report an observed heel initial contact within a step time window of the motion capture system, a miss or a false negative may be determined. Heel initial contacts detected by the algorithm, but not observed on the motion capture system, may be scored as a false positive detection. Finally, if neither the algorithm nor the motion capture system reports a heel initial contact, a true negative may be recorded. Using these measures, the algorithm may be shown to have a high sensitivity and specificity, where the term sensitivity probabilistically measures the algorithm's ability to correctly detect an observed step (i.e., true positives), whereas specificity characterizes the algorithm's ability to identify true negatives correctly. Heel initial contacts of left and right foot from forces-moments exerted on walker handles 108 may be determined with 97% sensitivity and 98% specificity (with a narrow 95% Confidence Interval of ±1%).

Figure 7:
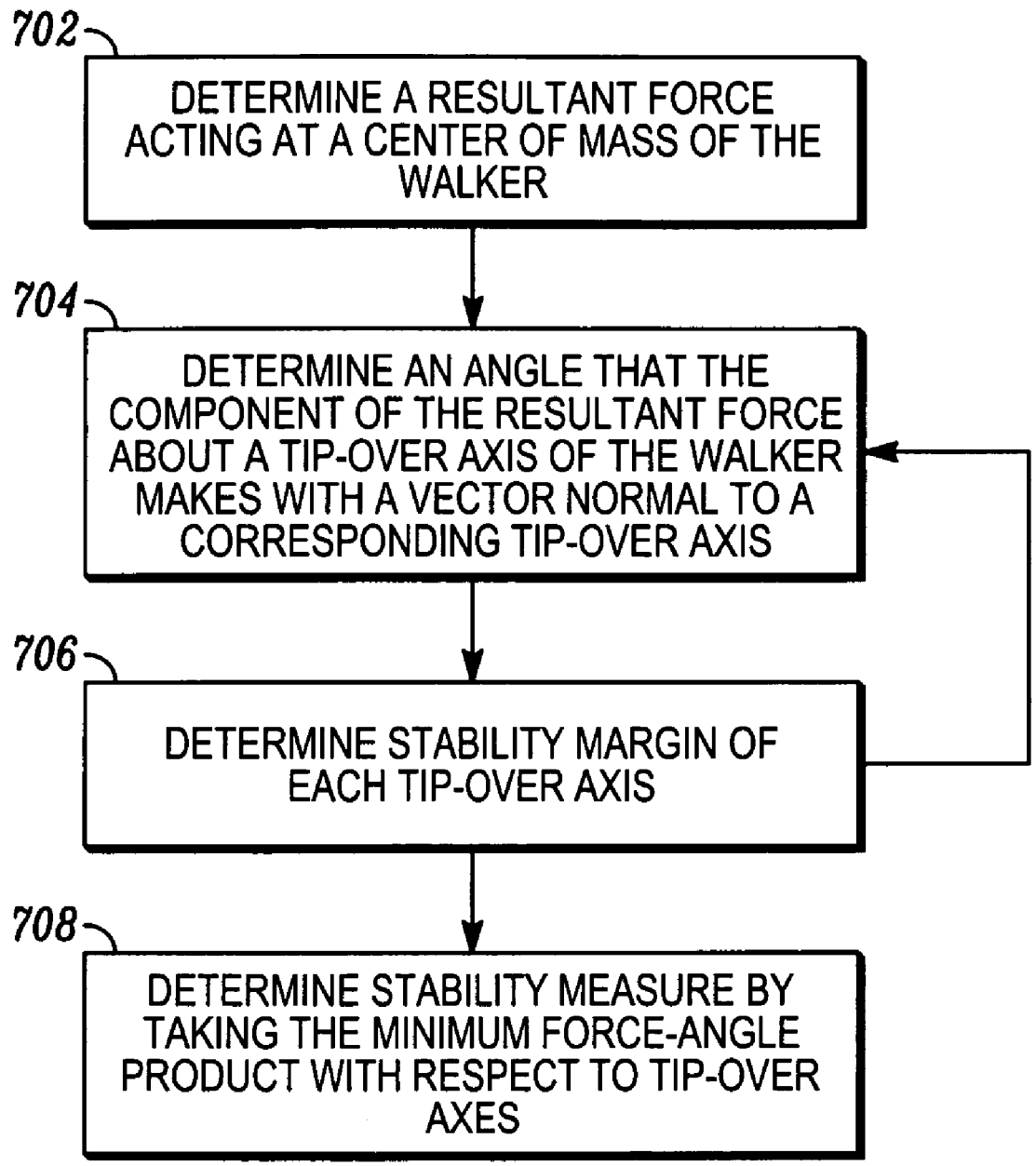
FIG. 7 is a flowchart illustrating an example of techniques for determining a stability measure of the instrumented walker of FIGS. 1-3.

FIG. 7 is a flowchart 700 illustrating an example of techniques for determining a stability measure of the instrumented walker 102. In FIG. 7, a force-angle stability measure considers a resultant force acting at a center of mass of the walker 102, determined from the sensor signals (702). An angle that the component of the resultant force about a tip-over axis of the walker makes with a vector normal to a corresponding tip-over axis also may be computed (704). For example, in a case where the ground contact points of the walker 102 form a triangular support base when projected onto the horizontal plane, then the three axes (each connecting two of the walker's three ground contact points) may be considered possible candidates to be a tip-over axis.

The resultant force on the walker's center of mass may be calculated by performing appropriate transformations on the measured external forces applied by the user and the gravitational load of the walker 102. The angular loads applied by the user also may be converted into an equivalent force couple for each tip-over axis.

Accordingly, Eq. (1) allows for a calculation of a stability measure for an $i^{th}$ tip-over axis (706):

$$\alpha(i) = [\theta(i)][F_r] \quad \text{Eq. (1)}$$

where $\theta(i)$ is the angle that the resultant force's component about the tip-over axis makes with the normal to the tip-over axis, and $F_r$ is the resultant force. This process may be repeated for each tip-over axis.

The overall force-angle stability measure of the walker 102 may then be calculated as the stability margin of the tip-over axis that has the minimum value of $\theta$ associated therewith (708). For example, Eq. (2) may be used to provide a global tip-over stability margin of the frame:

$$\alpha = [\min[\theta(i)]] F_r \quad \text{Eq. (2)}$$

In this formulation, then, a magnitude of a stability margin indicates a degree of stability of the system as a whole. As a result, higher positive values of a generally indicate a batter stability condition of the walker 102. When the a values approaches zero, the walker 102 may be considered to be under critical stability and be about to tip-over, whereas a tip-over may be considered to be in progress when a goes negative.

As a result, stability measures may be calculated instantaneously to evaluate a degree of stability during navigation. Further, the continuous tracking of the stability margin also informs a control system of a stability trend over a period of time. For example, a scenario in which a stability margin continuously decreases at a steep slope for a period of time (e.g., approximately half a second) may indicate the proximity of a probable tip-over.

Additionally, or alternatively, ground reaction forces associated with the walker 102 also may be analyzed to determine a stability index, and, thereby potential tip-over points. For example, if a ground reaction force is determined for each contact point of the walker 102 with the underlying ground surface using a standard rigid body model describing the frame, then the contact point with the minimum ground reaction force may be used to construct a stability index, on the assumption that this contact point would define a most-probable tip-over point.

Moreover, by determining a stability measure of the walker, or of a frame of the walker in association with a particular user, a corresponding user stability measure associated with the user may be inferred. For example, a given user may utilize the walker 102 for assistance in weight support, balance, or some combination thereof. By determining the walker stability measure as described above for a particular user, then, a characterization of the stability of that user may be obtained. For example, a first user may have very good balance, but may need the walker 102 because the user's legs cannot support a full weight of the user. Such a user may have a high stability rating. Conversely, a second user may have strong leg musculature, but may have an inner ear or other problem that leads to dizziness. Such a user may have a low stability rating. By knowing a user's stability rating, appropriate corrective action may be taken, either with respect to the type or implementation of the walker 102, or with respect to a diagnosis and treatment of the user in question.

The present description describes a device and method that passively assesses basic walker-assisted gait characteristics, including heel strikes and toe-off events, as well as stride time, double support, and right & left single support phases, using only force-moment measurements from the walker's handles. Additional gait characteristics, such as, for example, walking velocity, step length, stride length, and walker-user system stability also may be passively derived through the utilization of additional sensors.

The application of the instrumented walker and the described methods may be extended to longitudinal, outside the lab, gait assessment and monitoring. By providing in situ gait analysis technology as described herein, problems associated with routine clinical use of gait analysis (e.g., the manner in which gait laboratories are organized, tests are performed, and reports are generated, as well as the length of time and costs required for performing and interpreting tests) may be avoided.

Implementations also may be extended to other walker types, including, for example, back support walkers used by cerebral palsy patients and push-carts (such as strollers, shopping carts, and other devices used to enhance a mobility of a user, including able-bodied users requiring assistance to mobilize a weighted object for transport). Other types of mobility-assistance devices that are contemplated include, for example, two-wheeled slide walkers, three-wheeled walkers, four wheeled walkers, or any push-cart that requires the user to provide propulsion. The walker/cart may have active steering control, or a free wheeling castor, or a stepper motor (e.g., to control the steering direction of the front steering wheel).

A trajectory of the walker, as well as the user's motion in different navigational scenarios, also may be analyzed using the described instrumented walker, in attempt, for example, to understand a navigational intent of the user. Such navigational scenarios include, for example, walking in a straight line, or turning right and left at two different angles on each side.

In the various figures and in the description, it should be understood that various implementations may be implemented with a wide variety of special-purpose or general-purpose computing devices, systems, and configurations. Implementations may be implemented in computer-executable instructions designed for execution by a computing device. Implementations may be implemented as any combination of hardware, software, of firmware, as would be apparent.

While certain features of the described implementations have been illustrated as described herein, many modifications, substitutions, changes and equivalents will now occur to those skilled in the art. It is, therefore, to be understood that the appended claims are intended to cover all such modifications and changes.

What is claimed is:

1. A method comprising:
   receiving a plurality of sensor signals from a plurality of sensors associated with a mobility-assistance device operated on a surface by a user, including receiving a left sensor signal from a left sensor attached to a left side handle of the mobility assistance device, and receiving a right sensor signal from a right sensor attached to a right side handle of the mobility assistance device;
   relating the plurality of sensor signals to a contact attribute associated with a contact of the user with the surface, including estimating an approximate time of the contact attribute including a foot initial contact, using a peak signal representing a summation of right and left sensor signals; and
   determining a gait characteristic of the user, based on the contact attribute.

2. The method of claim 1 wherein receiving the plurality of sensor signals from the plurality of sensors comprises receiving a force signal associated with a force exerted by the user on the mobility assistance device.

3. The method of claim 1 wherein relating the plurality of sensor signals to a contact attribute comprises relating the plurality of sensor signals to a foot-off contact of a foot of the user from the surface.

4. The method of claim 1 wherein relating the plurality of sensor signals to a contact attribute comprises correlating gait-related signal variations of the plurality of sensor signals with the contact attribute.

5. The method of claim 1 wherein relating the plurality of sensor signals to a contact attribute comprises:
   determining a peak of the plurality of sensor signals; and
   correlating the peak with the contact attribute.

6. The method of claim 1 wherein determining the gait characteristic of the user comprises determining one or more of a group of gait characteristics that includes a gait step count, a gait pace, or timing information of different gait phases.

7. The method of claim 1 wherein determining the gait characteristic of the user comprises determining the gait characteristic based on a supplemental sensor signal from a supplemental sensor associated with the mobility assistance device.

8. The method of claim 7 wherein determining the gait characteristic of the user comprises determining one or more of a group of gait characteristics that includes an instantaneous walking velocity, an average walking velocity, a step length of the user, or a stride length of the user.

9. The method of claim 1 wherein determining the gait characteristic of the user comprises determining a stability measure of the mobility assistance device.

10. The method of claim 1 comprising performing a longitudinal analysis based on the gait characteristic.

11. The method of claim 10 wherein performing the longitudinal analysis comprises:
    collecting data associated with the gait characteristic over a time period; and
    performing a trend analysis on the data.

12. A system comprising:
    a data acquisition system that is operable to receive a plurality of sensor signals from a plurality of sensors associated with a mobility assistance device; and
    a use analyzer that is operable to relate the plurality of sensor signals to a contact attribute associated with a contact of a user of the mobility assistance device with an underlying surface, and further operable to determine a gait characteristic of the user, based on the contact attribute,
    wherein the data acquisition system is configured to receive a left sensor signal from a left sensor attached to a left side handle of the mobility assistance device, and to receive a right sensor signal from a right sensor attached to a right side handle of the mobility assistance device, and wherein the use analyzer is configured to estimate an approximate time of the contact attribute including a foot initial contact, using a peak signal representing a summation of right and left sensor signals.

13. The system of claim 12 wherein the plurality of sensors comprise at least one of a force or moment sensor.

14. The system of claim 12 wherein the contact attribute comprises a foot-off contact of the user from the surface.

15. The system of claim 12 wherein the use analyzer is operable to relate the plurality of sensor signals to the gait characteristic by implementing a peak detection algorithm on the plurality of sensor signals.

16. The system of claim 12 wherein the data acquisition system is configured to receive the plurality of sensor signals including receiving a velocity-related sensor signal associated with a velocity of movement of the mobility assistance device.

17. The system of claim 12 wherein the data acquisition system is configured to receive the plurality of sensor signals including receiving a distance-related sensor signal associated with a distance of movement of the mobility assistance device.

18. The system of claim 12 wherein the use analyzer is configured to relate the plurality of sensor signals to the contact attribute including associating the contact with either a left leg or a right leg of the user.

19. The system of claim 12 wherein the use analyzer is configured to analyze the left sensor signal to associate the foot initial contact with a left foot of the user.

20. A system comprising:
a mobility assistance device;
a plurality of sensors attached to the mobility assistance device and operable to convert an operational action of a user of the mobility assistance device into a plurality of sensor signals; and
a use analyzer that is operable to relate the plurality of sensor signals to a contact attribute associated with a contact of the user of the mobility assistance device with an underlying surface, and further operable to determine a gait characteristic of the user, based on the contact attribute,
wherein the use analyzer is configured to receive a left sensor signal from a left sensor attached to a left side handle of the mobility assistance device, and to receive a right sensor signal from a right sensor attached to a right side handle of the mobility assistance device, and configured to estimate an approximate time of the contact attribute including a foot initial contact, using a peak signal representing a summation of right and left sensor signals.

21. The system of claim 20 wherein the plurality of sensors comprise at least one of a force or moment sensor.

22. The system of claim 20 wherein the contact attribute comprises a foot-off contact of the user from the surface.

23. A computer program product tangibly embodied on a non-transitory computer-readable medium and encoding a computer program for executing on a computing device a computer process, the computer process comprising:
receiving a plurality of sensor signals from a plurality of sensors associated with a mobility-assistance device operated on a surface by a user, including receiving a left sensor signal from a left sensor attached to a left side handle of the mobility assistance device, and receiving a right sensor signal from a right sensor attached to a right side handle of the mobility assistance device;
relating the plurality of sensor signals to a contact attribute associated with a contact of the user with the surface, including estimating an approximate time of the contact attribute including a foot initial contact, using a peak signal representing a summation of right and left sensor signals; and
determining a gait characteristic of the user, based on the contact attribute.

24. The computer program product of claim 23 wherein the plurality of sensors comprise at least one of a force or moment sensor.

25. The computer program product of claim 23 wherein the contact attribute comprises a foot-off contact of the user from the surface.

* * * * *